United States Patent
Tada et al.

(10) Patent No.: US 7,199,262 B2
(45) Date of Patent: Apr. 3, 2007

(54) 3-HYDROXYPROPYL ESTER OF 2-TRIFLUOROMETHYLACRYLIC ACID AND PROCESS FOR PRODUCING SAME

(75) Inventors: Takahisa Tada, Saitama (JP); Seiji Murata, Saitama (JP); Akihiro Fukui, Saitama (JP); Junji Negishi, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 146 days.

(21) Appl. No.: 11/152,144

(22) Filed: Jun. 15, 2005

(65) Prior Publication Data

US 2006/0009653 A1    Jan. 12, 2006

(30) Foreign Application Priority Data

Jun. 16, 2004 (JP) .............................. 2004-177983

(51) Int. Cl.
*C07C 69/52* (2006.01)
*C07C 69/34* (2006.01)
*C07C 69/63* (2006.01)

(52) U.S. Cl. ................ 560/223; 560/201; 560/227

(58) Field of Classification Search ........... 560/223, 560/201, 227, 226, 219
See application file for complete search history.

(56) References Cited

U.S. PATENT DOCUMENTS 7,060,771 B2 * 6/2006 Komoriya et al. ......... 526/245

FOREIGN PATENT DOCUMENTS

| JP | 57104906 | 6/1982 |
| JP | 58018608 | 2/1983 |
| JP | 3041051 | 2/1991 |
| JP | 2004083730 | 3/2004 |

* cited by examiner

*Primary Examiner*—Karl Puttlitz
(74) *Attorney, Agent, or Firm*—Crowell & Moring LLP

(57) ABSTRACT

The invention relates to a novel compound, 3-hydroxypropyl ester of 2-trifluoromethyl acrylic acid, represented by the formula [1]. The invention further relates to a process for producing the compound. This process includes reacting 2-trifluoromethylacrylic halide represented by the formula [2], wherein the halogen atom is F or Cl, with 1,3-propanediol represented by the formula [3], in the presence of a base

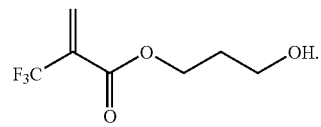

[1]

19 Claims, No Drawings

3-HYDROXYPROPYL ESTER OF 2-TRIFLUOROMETHYLACRYLIC ACID AND PROCESS FOR PRODUCING SAME

BACKGROUND OF THE INVENTION

The present invention relates to a novel compound, 3-hydroxypropyl ester of 2-trifluoromethylacrylic acid, represented by the after-mentioned formula [1], and its production process. This 3-hydroxypropyl ester can also be named 3-hydroxypropyl 2-(trifluoromethyl)acrylate.

Fluorine-containing compounds have been used or developed in various fields particularly in the field of advanced materials due to their good qualities (e.g., water repellency, oil repellency, low water absorption, heat resistance, weather resistance, corrosion resistance, transparency, photosensitivity, low refractive index, and low dielectric property). In particular, they are used in the coating field in view of their characteristic transparency behavior in each wavelength. Recently, there have been active researches and developments of (a) anti-reflection films taking advantage of their low refractive indexes and visible light transparency, (b) optical devices taking advantage of their transparency in long wavelength band (optical communication wavelength band), and (c) resist compositions taking advantage of their transparency in ultraviolet region (particularly vacuum ultraviolet region).

A common aim in polymer design of such researches and developments is to achieve good adhesion to substrate and high glass transition point (hardness), while achieving transparency in each wavelength for use by introducing as many fluorine atoms as possible. There are various proposals of increasing transparency at each wavelength by increasing the fluorine content in material design. However, there are few reports on improving fluorine-containing monomers themselves in hydrophilicity and adhesion and on obtaining high glass transition point.

Acrylic and methacrylic esters have an ethylenic unsaturated bond in the molecule and are widely used as raw materials for producing polymers, in various fields such as paint, adhesive, ink, resist material and paper-processing agent (see Japanese Patent Laid-open Publication JP-A-3-41051). Acrylic and methacrylic esters containing a hydroxyl group in the ester chain exhibit a good hydrophilicity. Therefore, they are used as a raw material for producing contact lens and anti-fogging lens plastics. Furthermore, they have recently been used as a dripping inhibitor of flame-retardant pressure sensitive adhesive tapes (see JP-A-2004-083730).

Fluorinated acrylic and methacrylic esters are used mainly in the fields of photochemistry and radiation chemistry (see JP-A-57-104906 and JP-A-58-018608). Polyacrylate and polymethacrylate, which contain a trifluoromethyl group in an acyl moiety in the molecule, have a less degree of cross-linking, as compared with non-fluorinated compounds, and thus used as a positive resist material. (see T. G. Tessier, et al., Polymer Engineering & Science, pp. 1,000 (1983)).

Hitherto, there have not been sufficient examinations as to whether or not acrylic and methacrylic esters, which have a trifluoromethyl group in the acyl moiety of their molecule and a hydroxyl group at the end of the ester chain, are effective as functional materials. As a compound having a trifluoromethyl group in the acyl moiety of the molecule and a hydroxyl group at the end of the ester chain, there is known 2-hydroxyethyl ester of 2-trifluoromethylacrylic acid (2-hydroxyethyl 2-(trifluoromethyl)acrylate) represented by the formula [4] (Registry Number: 450358-94-8 in Chemical Abstracts Service (CAS)).

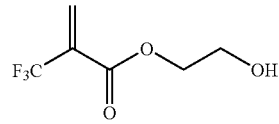

[4]

However, the production process and the use of this compound have not been reported.

SUMMARY OF THE INVENTION

It is an object of the present invention to provide a novel compound that has a trifluoromethyl group in an acyl moiety of the molecule and a hydroxyl group at the end of an ester chain and that is useful as a functional material (e.g., resist material).

It is another object of the present invention to provide a process for producing the novel compound in an industrially advantageous way.

As mentioned above, there is known a compound, 2-hydroxyethyl ester of 2-trifluoromethylacrylic acid represented by the formula [4]. However, this compound is found only in the CAS search. Its production process has not been reported, and it has not been available in a commercial way.

In fact, 2-hydroxyethyl ester of 2-trifluoromethylacrylic acid represented by the formula [4] is low in stability, and its isolation is difficult. Specifically, when a mixture containing this compound is subjected to a vacuum distillation even under a minimum heated condition, a wide variety of decomposition reactions occur, thereby producing large amounts of by-products that are difficult of separation.

Thus, there has been a demand for finding a novel compound that has a trifluoromethyl group in an acyl moiety in the molecule and a hydroxyl group at the end of the ester chain and that is suitable for practical use and is stable. Furthermore, there has been a demand for finding a process for industrially producing such compound.

In view of the above-mentioned problems, the present inventors have eagerly conducted a research for finding such a useful compound that has a trifluoromethyl group in an acyl moiety in the molecule and a hydroxyl group at the end of the ester chain. As a result, we have found that 3-hydroxypropyl ester of 2-trifluoromethylacrylic acid, represented by the following formula [1], which has a structure in which one methylene chain has been added to the compound represented by the formula [4], is high in thermal stability, can efficiently be synthesized from a raw material of low price, and can efficiently be isolated from the obtained reaction mixture by a special process.

According to the present invention, there is provided a novel compound, 3-hydroxypropyl ester of 2-trifluoromethyl acrylic acid, represented by the formula [1].

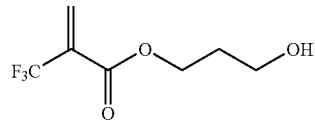

[1]

According to the present invention, there is provided a process for producing 3-hydroxypropyl ester of 2-trifluoromethyl acrylic acid, represented by the formula [1]. This process comprises the step of (a) reacting 2-trifluoromethylacrylic halide represented by the formula [2],

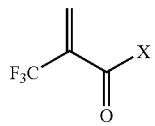

[2]

wherein X represents F or Cl, with 1,3-propanediol represented by the formula [3],

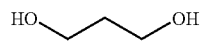

[3]

in the presence of a base.

DETAILED DESCRIPTION

It is possible to efficiently produce the target compound (represented by the formula [1]) by the above step (a) of the process. We have unexpectedly found that, in contrast with 2-hydroxyethyl ester of 2-trifluoromethylacrylic acid represented by the formula [4], the target compound can be isolated as a high-purity compound (purity: 90% or greater) by the step of (b) distilling a reaction mixture obtained by the step (a), under reduced pressure.

Furthermore, we have unexpectedly found that the unreacted 1,3-propanediol and the like coexistent with the target compound can efficiently be removed from the system by the step of (c) washing a distillate (main distillate) obtained by the step (b) with water, thereby producing the target compound with particularly good selectivity and particularly good yield.

In the process for producing the target compound, the step (a) of the target reaction is essential. In contrast, the steps (b) and (c) are optional steps for obtaining the target compound with high purity.

We further have found that the target compound can preferably be produced by conducting each of the above steps under the after-mentioned specific conditions.

The target compound of the invention, 3-hydroxypropyl ester of 2-trifluoromethyl acrylic acid, represented by the formula [1], has the following unique characteristics, as compared with the above-mentioned known compound, 2-hydroxyethyl ester of 2-trifluoromethylacrylic acid represented by the formula [4]. Firstly, the 3-hydroxypropyl ester can more easily be produced, as compared with the 2-hydroxyethyl ester. Secondly, the 3-hydroxypropyl ester has a propyl group as a side chain, which is longer by a distance of one carbon atom than the ethyl group of the 2-hydroxyethyl ester. That is, not only in case that the 3-hydroxypropyl ester is polymerized into a homopolymer, but also in case that the 3-hydroxypropyl ester is copolymerized with another monomer having a long side chain length, the hydroxyl group at the side chain terminal of the 3-hydroxypropyl ester can effectively function as a reactive functional group in curing reaction and the like. The resulting polymer can have low glass transition temperature due to the length of the side chain, thereby softening the polymer. Thirdly, the propyl group lowers polarity further than the ethyl group does. Thus, a polymer resulting from the 3-hydroxylpropyl ester can have a higher solubility in organic solvents and can improve transparency in the ultraviolet region.

Therefore, the 3-hydroxypropyl ester is useful in terms of, for example, synthesis, chain length, and polarity, as mentioned above. In particular, the chain length of the propyl group improves freedom of molecular design. Thus, the 3-hydroxypropyl ester can preferably be used as a raw material monomer for electronic materials, optical materials, biochemical materials and the like, which are characterized in water solubility, alkali solubility, cross-linking property, photosensitivity, ultraviolet transparency, heat resistance, adhesion, softness and the like.

In the following, the step (a) is described in detail. A raw material of the step (a), 2-trifluoromethylacrylic halide represented by the formula [2] is specifically limited to 2-trifluoromethylacrylic fluoride or 2-trifluoromethylacrylic chloride. Although either one can preferably be used, 2-trifluoromethylacrylic chloride (X=Cl in the formula [2]) is more preferable.

The mixing ratio of 2-trifluoromethylacrylic halide represented by the formula [2] to 1,3-propanediol represented by the formula [3] is not particularly limited. However, 1,3-propanediol has two hydroxyl groups in the molecule. Thus, a by-product (diester) tends to be formed by an esterification of two hydroxyl groups of 1,3-propanediol by an excess of 2-trifluoromethylacrylic halide in the system. In order to improve yield of the target compound, it is preferable to maintain an excess of 1,3-propanediol in the system during the reaction, relative to 2-trifluoromethylacrylic halide.

For this, it is particularly preferable to conduct a process by putting 1,3-propanediol into a reactor and then intermittently or continuously introducing 2-trifluoromethylacrylic halide into the reactor. With this process, it is possible to prevent the formation of the diester and to obtain the 3-hydroxypropyl ester in high yield. Hereinafter, this process may be referred to as "continuous process".

Since the reaction of the step (a) is an exothermic reaction, a strong heat generation tends to occur by conducting the reaction in an industrial scale. In order to control this heat generation, it is also effective to conduct the continuous process.

It is more preferable to conduct the reaction of the step (a) by diluting the reactant(s) with inert solvent(s). With this, it becomes possible to easily control the reaction and to improve selectivity and yield of the target compound. The solvent is not limited to particular types. The amount of the solvent may be 1–20 g, preferably 2–10 g, more preferably 3–8 g, per gram of 2-trifluoromethylacrylic halide. If the solvent is in a range of 1–20 g, a hydrochloride or hydrofluoride (salt) of the base (e.g., lutidine), which is produced as a by-product during the reaction, takes a good slurry form. Therefore, it is possible to have a particularly good operability as well as good reactivity.

In the case of conducting the continuous process, it is preferable to introduce 2-trifluoromethylacrylic halide diluted with the solvent. With this, the reaction proceeds rapidly and smoothly. The solvent to be used for diluting 2-trifluoromethylacrylic halide may be in an amount of 0.1–5 g, preferably 0.3–3 g, more preferably 0.5–1.5 g, per gram of 2-trifluoromethylacrylic halide. In this case, it is preferable to suitably set the amount of the organic solvent such that the total amount of the organic solvent in the reaction system after the introduction of 2-trifluoromethylacrylic halide diluted with the organic solvent is in the above-mentioned range. Although the reaction of the step (a) proceeds with no solvent, it may cause a demerit(s), such as necessity to introduce 2-trifluoromethylacrylic halide into the system at a very slow rate, since the reaction rate is slow.

The introduction (dropping) rate of a 2-trifluoromethylacrylic halide solution prepared by diluting 2-trifluoromethylacrylic halide with an inert solvent may be 1.5–10 g, preferably 3–9 g, more preferably 5-7.5 g, per hour, relative to 100 g of 1,3-propanediol. The solvent to be used in the step (a) is not particularly limited. Its particularly preferable solvents include ethers such as diethyl ether, methyl-t-butyl ether, methyl isopropyl ether, ethyl isopropyl ether, diisopropyl ether, tetrahydrofuran, dioxane, and tetrahydropyran, since these solvents are highly capable of dissolving 2-trifluoromethylacrylic halide and hardly participate in the reaction. These solvents may be used singly or in combination.

The molar or equivalent ratio of the total amount of 1,3-propanediol to that of 2-trifluoromethylacrylic halide depends on at which rate 2-trifluoromethylacrylic halide is introduced intermittently or continuously into the system. However, the total amount of 1,3-propanediol can be in excess of that of 2-trifluoromethylacrylic halide, in order to obtain the target compound with high selectivity and high yield. More specifically, the total amount of 1,3-propanediol is preferably 1–40 moles (equivalents), more preferably 10–30 moles (equivalents), still more preferably 15–25 moles (equivalents), relative to 1 mol (equivalent) of 2-trifluoromethylacrylic halide (see Example 2).

Even if 1,3-propanediol is used in excess in the reaction of the step (a), it can be separated and reused by the distillation of the step (b). Therefore, its use in excess is not necessarily an economical demerit. From the viewpoints of yield of the target compound and the operation time, it is advantageous to use 1,3-propanediol in excess.

If the total amount of 1,3-propanediol exceeds 40 moles relative to 1 mol of 2-trifluoromethylacrylic halide, the volume required for carrying out the reaction may become too large. This is not preferable from the viewpoint of productivity.

The base to be used in the step (a) may preferably be at least one selected from trimethylamine, triethylamine, pyridine, 2,6-dimethylpyridine (2,6-lutidine), dimethylaminopyridine, sodium carbonate, potassium carbonate, sodium hydroxide, and potassium hydroxide. Of these, pyridine and 2,6-dimethylpyridine can particularly preferably be used. With this, the reactivity becomes good. Furthermore, operability becomes good, since the use of these two bases results in the precipitation of hydrochlorides or hydrofluorides (salts) of these bases with easy filtration property. In the case of using the continuous process, it is preferable to firstly mix the base with 1,3-propanediol. It is not preferable to firstly mix the base with 2-trifluoromethylacrylic halide, since 2-trifluoromethylacrylic halide may be decomposed by a contact with the base for a long time.

The amount of the base may be 1.0–5.0 moles, preferably 1.05–2.0 moles, more preferably 1.1–1.3 moles, per mol of 2-trifluoromethylacrylic halide. If the base is less than 1.0 mol per that, both of the reaction selectivity and the target compound yield may become too low. If the base is greater than 5.0 moles per that, the amount of the base that does not participate in the reaction may become too much. This may not economically be preferable.

The base may be an aromatic organic base, such as pyridine, 2,6-dimethylpyridine, and dimethylaminopyridine. In this case, the reaction proceeds smoothly, even if the aromatic organic base is in small excess of 2-trifluoromethylacrylic halide. The unreacted portion of these organic bases can be removed as the initial distillate by conducting the distillation operation of the step (b). In case that the base is the aromatic organic base, the amount of the base is preferably 1.0–2.0 moles, more preferably 1.1–1.3 moles, per mol of 2-trifluoromethylacrylic halide.

The reaction temperature of the step (a) may be in a range of −50° C. to +50° C., preferably −30° C. to +10° C., more preferably −20° C. to 0° C. If it is lower than −50° C., the reaction rate may become too low. This is not preferable as a practical production process. If it is higher than +50° C., selectivity and yield of the target compound may become too low.

In the step (a), it is optional to conduct the reaction in the presence of a polymerization inhibitor for the purpose of suppressing polymerization of 2-trifluoromethylacrylic halide or the product, 3-hydroxypropyl ester of 2-trifluoromethyl acrylic acid. The polymerization inhibitor may be at least one compound selected from 2,5-di-t-butylhydroquinone, 1,2,4-trihydroxybenzene, 2,5-bistetramethylbutylhydroquinone, leucoquinizarin, phenothiazine, tetraethylthiuram, disulfide, 1,1-diphenyl-2-picrylhydrazyl, and 1,1-diphenyl-2-picrylhydrazine. Further examples of the polymerization inhibitor expressed in trade name, together with compound name in parenthesis, include NONFLEX F (N,N'-di-2-naphthyl-p-phenylenediamine), NONFLEX H (N,N'-diphenyl-p-phenylenediamine), NONFLEX DCD (4,4'-bis($\alpha,\alpha'$-dimethyl benzyl)diphenylamine), NONFLEX MBP (2,2'-methylene-bis(4-methyl-6-tert-butylphenol), and OZONONE 35 (N-(1-methylheptyl)-N'-phenyl-p-phenylenediamine) of SEIKO CHEMICAL Co., Ltd located in Japan, and Q-1300 (N-nitrosophenylhydroxylamine ammonium salt) and Q-1301 (N-nitrosophenylhydroxylamine alminium salt) of Wako Pure Chemical Industries, Ltd. located in Japan. All of the above examples of the polymerization inhibitor are easily available as commercial products.

The polymerization inhibitor may be in an amount of 0.000005 to 0.1 moles, preferably 0.00001 to 0.05 moles, more preferably 0.0001 to 0.01 moles, per mol of 2-trifluoromethylacrylic halide. Even if it exceeds 0.1 moles per that, the effect of suppressing the polymerization may not improve further. Thus, this may be economically not preferable.

Although the time required for completing the step (a) is not particularly limited, it may be 3 to 5 hours. It may depend on the reaction temperature and other conditions. It is preferable to terminate the reaction at the time when the raw material has sufficiently been consumed and when the target compound has sufficiently been produced, while analyzing the composition of the reaction liquid at suitable timings by gas chromatography or the like.

The step (b) is described in detail in the following. In the step (b), a reaction mixture obtained by the step (a) is distilled under reduced pressure to recover the target 3-hydroxypropyl ester as a main distillate. Since the 3-hydroxypropyl ester is high in thermal stability, it is hardly decomposed by distillation. Therefore, it is possible to recover the 3-hydroxypropyl ester with high purity.

The distillation of the step (b) is conducted preferably under reduced pressure to lower the temperature. The pressure can be 2,400 Pa or lower, preferably 1,200 Pa or lower, more preferably 800 Pa or lower. If it is higher than 2,400 Pa, the required temperature may become too high. If it is lower than 50 Pa, the each component separation efficiency by the distillation may become too low, and high-boiling-point compounds tend to remain in the main distillate.

In the step (b), it is preferable to directly distill the reaction mixture obtained by the step (a), without conducting any purification operation before the distillation. After completing the reaction of the step (a), the unreacted raw material 1,3-propanediol remains in the system. In particular, a large amount of 1,3-propanediol remains in the reaction mixture, in case that the reaction of the step (a) is conducted by using an excess amount of 1,3-propanediol.

It is considered to mix water with a reaction mixture obtained by the step (a) to wash the reaction liquid with water and thereby remove the remaining 1,3-propanediol. In this case, however, the boundary between the organic and aqueous layers may become unclear. With this, the target compound may become low in recovery. In contrast with this, a reaction mixture obtained by the step (a) can directly be distilled. With this, an excess of 1,3-propanediol almost remains in the reactor, since it is a high-boiling-point distillate. Thus, in case that the step (a) is conducted by using an excess of 1,3-propanediol, it is particularly effective to directly conduct the step (b) without conducting a particular purification operation.

During the distillation of the step (b), the solvent used in the step (a) is firstly distilled out, and then low-boiling-point substances (e.g., acrylic acid) are distilled out. Then, the target 3-hydroxypropyl ester is recovered as a main distillate.

Even after the distillation of the step (b), a small amount of 1,3-propanediol may remain in the distillate. Such 1,3-propanediol can efficiently be removed by the step (c).

It is preferable to conduct the step (b), while the pressure and the distillation tower top temperature are controlled and while the distillate composition is analyzed at a suitable timing by gas chromatography or the like.

The step (c) is described in detail in the following. In the step (c), water is added to the main distillate obtained by the step (b) to wash the same. It is possible by the step (c) to efficiently transfer or extract 1,3-propanediol from the main distillate into the aqueous layer.

It is possible to conduct the step (c) by adding water to the main distillate obtained by the step (b), followed by stirring to have separated organic and aqueous layers. The separation of these layers becomes easy by adding a water-insoluble organic solvent. Although this solvent is not particularly limited, its preferable examples include ethers (e.g., diethyl ether and diisopropyl ether), chlorine-containing solvents (e.g., methylene chloride, chloroform, and carbon tetrachloride), and aromatic solvents (e.g., benzene, toluene, and xylene).

The amounts of water and water-insoluble solvent to be used in the step (c) are not particularly limited. For example, each of water and water-insoluble solvent may be 1 g per 1 g of the main distillate obtained by the step (b).

It is preferable to terminate the step (c) at the time when 1,3-propanediol has completely been removed, while analyzing the composition of the separated organic layer by gas chromatography or the like.

The organic layer obtained by the operation of the step (c) contains the 3-hydroxypropyl ester as a main component and water used in the washing of the step (c). This water can be removed by a conventional method such as distillation or desiccation with desiccant.

A process for producing the 3-hydroxypropyl ester may be specifically conducted in accordance with a preferred embodiment of the present invention, as follows.

Firstly, a reactor proof against the reaction conditions is charged with the base, the solvent, 1,3-propanediol represented by the formula [2], and the polymerization inhibitor, followed by maintaining the reaction solution at a temperature of from $-10°$ C. to $0°$ C. 2-trifluoromethylacrylic halide is added in a dropwise manner by spending a predetermined time. Then, the termination of the reaction is checked by monitoring the consumption of the raw material (2-trifluoromethylacrylic halide), followed by aging for 1 hr and then raising the temperature of the reaction liquid to room temperature.

The resulting reaction liquid is directly distilled under reduced pressure. This distillation is conducted by taking care of the degree of the pressure reduction in order to maintain the reactor temperature at $130°$ C. or lower. A distillate is separated, based on the analytical results of gas chromatography and tower top temperature. Since the resulting main distillate contains a small amount of 1,3-propanediol, it is washed with water preferably by using a water-insoluble solvent (e.g., isopropyl ether). After that, it is possible to obtain the target compound 3-hydroxypropyl ester with high purity by removing the solvent through a conventional method such as distillation. According to need, water can also be removed by a conventional method such as dehydration.

The following nonlimitative examples are illustrative of the present invention. Herein, the percent (%) of the compositional analysis value refers to areal % of an organic component obtained by gas chromatography of a sampled reaction mixture.

EXAMPLE 1

Production of 3-Hydroxypropyl Ester of 2-Trifluoromethylacrylic Acid

A 500 ml three-necked flask equipped with a thermometer and a reflux condenser was charged with a stirring magnet covered with tetrafluoroethylene resin, 200.0 g (2.63 mol) of 1,3-propanediol, 15.5 g (0.14 mol) of 2,6-lutidine, 120 mL (106.6 g) of tetrahydrofuran (THF), 0.06 g (0.3 wt %) of NONFLEX MBP as a polymerization inhibitor, followed by adding a solution, which has been prepared by mixing 20.8 g (0.13 mol) of 2-trifluoromethylacrylic chloride with 20.8 g of THF, in a dropwise manner with stirring with a stirrer at a temperature range of $-9°$ C. to $-7°$ C. for 3 hr. After this addition, the stirring was conducted for 1 hr at this temperature range. After that, the reaction liquid was analyzed by gas chromatography. With this, it was found to contain 75.3% of the target 3-hydroxypropyl ester, 0.6% of a diester as a by-product, and 24.1% of others. The raw material 2-trifluoromethylacrylic chloride was not detected. After distilling the solvent out, a distillation was conducted under reduced pressure (0.6–0.8 kPa) to collect a distillate of 86–90° C. With this, 29.48 g of a crude 3-hydroxypropyl ester were obtained. Then, 30 g of isopropyl ether and then 30 g of water were added to remove 1,3-propanediol from the distillate. After that, the solvent was distilled out, thereby obtaining 11.2 g of the 3-hydroxypropyl ester. This product was found by gas chromatography to contain 96.1% of the target 3-hydroxypropyl ester and 3.9% of others. The raw material 2-trifluoromethylacrylic chloride was not detected. The yield was 42.9%. The NMR data of the target compound were as follows.

$^1$H NMR (solvent: CDCl$_3$; standard substance TMS); δ6.74 (s, 1H), 6.45 (s, 1H), 4.42 (t, J=6.10 Hz, 2H), 3.74 (t, J=5.85 Hz, 2H), 2.02 (s, 1H), 1.99–1.931 (m, 2H). 19F NMR (solvent: CDCl$_3$; standard substance: CDCF$_3$); δ–66.09 (s, 3F).

EXAMPLE 2

Production of 3-hydroxypropyl Ester of 2-trifluoromethylacrylic Acid

A 100 ml three-necked flask equipped with a thermometer and a reflux condenser was charged with a stirring magnet covered with tetrafluoroethylene resin, 4.4 g (0.058 mol) of 1,3-propanediol, 3.4 g (0.032 mol) of 2,6-lutidine, 22 mL (19.6 g) of THF, 0.015 g (0.3 wt %) of NONFLEX MBP as a polymerization inhibitor, followed by adding a solution, which has been prepared by mixing 5.0 g (0.029 mol) of 2-trifluoromethylacrylic chloride with 5.0 g of THF, in a dropwise manner with stirring with a stirrer at a temperature range of –9° C. to –7° C. for 1 hr. After this addition, the stirring was conducted for 1 hr at this temperature range. After that, the reaction liquid was analyzed by gas chromatography. With this, it was found to contain 70.1% of the target 3-hydroxypropyl ester, 9.2% of a diester as a by-product, and 20.7% of others. The raw material 2-trifluoromethylacrylic chloride was not detected.

REFERENTIAL EXAMPLE

Production of 2-hydroxyethyl Ester of 2-trifluoromethylacrylic Acid

A 500 ml three-necked flask equipped with a thermometer and a reflux condenser was charged with a stirring magnet covered with tetrafluoroethylene resin, 37.2 g (0.60 mol) of ethylene glycol, 35.4 g (0.33 mol) of 2,6-lutidine, 250 mL (222 g) of THF, and 0.25 g (0.5 wt %) of NONFLEX MBP as a polymerization inhibitor, followed by adding 50.0 g (0.13 mol) of 2-trifluoromethylacrylic chloride in a dropwise manner with stirring with a stirrer at a temperature range of –2° C. to 0° C. for 6 hr. After this addition, the stirring was conducted for 1 hr at this temperature range. After that, the reaction liquid was sampled, followed by adding isopropyl ether and then water to wash the reaction liquid. The resulting solution was analyzed by gas chromatography. With this, it was found to contain 38.6% of the target 2-hydroxyethyl ester and 61.4% of others. The raw material 2-trifluoromethylacrylic chloride was not detected. 100 g of isopropyl ether were added to the reaction liquid, followed by adding 100 g of water to wash the reaction liquid. The resulting organic layer was washed again with 100 g of water. After confirming the complete removal of ethylene glycol, the solvent was distilled out. Then, a distillation was conducted under reduced pressure (0.6–0.8 kPa) to collect a distillate of 68–70° C. With this, however, the separation of the target compound was not successful. In fact, although the target compound 2-hydroxyethyl ester was obtained, its decomposition occurred. Furthermore, a peak of ethylene glycol was found. The obtained main distillate of 10.1 g was found to contain 33.5% of the target compound 2-hydroxyethyl ester, 16.1% of ethylene glycol, and 50.4% of others. The raw material 2-trifluoromethylacrylic chloride was not detected.

Noticeable decomposition reactions have occurred during the distillation operation in Reference Example. Thus, it was not possible to obtain the target compound 2-hydroxyethyl ester with high purity.

The entire contents of Japanese Patent Applications P2004-177983 (filed Jun. 16, 2004), of which priority is claimed in the present application, are incorporated herein by reference.

What is claimed is:

1. 3-hydroxypropyl ester of 2-trifluoromethyl acrylic acid, represented by the formula [1]

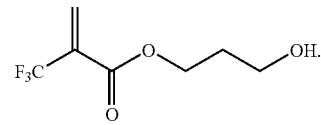

2. A process for producing 3-hydroxypropyl ester of 2-trifluoromethyl acrylic acid, represented by the formula [1],

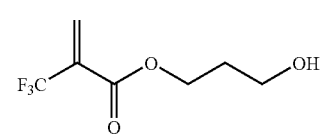

the process comprising reacting 2-trifluoromethylacrylic halide represented by the formula [2]

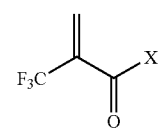

wherein X represents F or Cl, with 1,3-propanediol represented by the formula [3],

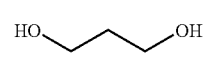

in the presence of a base.

3. A process according to claim 2, wherein X of the formula [2] represents Cl.

4. A process according to claim 2, wherein the reacting is conducted by using the 1,3-propanediol in an excessive amount relative to the 2-trifluoromethylacrylic halide.

5. A process according to claim 2, wherein the reacting is conducted by putting the 1,3-propanediol into a reactor and then by intermittently or continuously adding the 2-trifluoromethylacrylic halide into the reactor.

6. A process according to claim 5, wherein the 2-trifluoromethylacrylic halide is diluted with an inert solvent, prior to the reacting.

7. A process according to claim 2, wherein the base is at least one selected from the group consisting of trimethylamine, triethylamine, pyridine, 2,6-dimethylpyridine, dimethylaminopyridine, sodium carbonate, potassium carbonate, sodium hydroxide, and potassium hydroxide.

8. A process according to claim 7, wherein the base is at least one of pyridine and 2,6-dimethylpyridine.

9. A process according to claim 2, wherein the reacting is conducted in the presence of a polymerization inhibitor.

10. A process for producing 3-hydroxypropyl ester of 2-trifluoromethyl acrylic acid, represented by the formula [1],

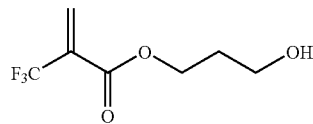

the process comprising the steps of
(a) reacting 2-trifluoromethylacrylic halide represented by the formula [2]

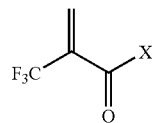

wherein X represents F or Cl, with 1,3-propanediol represented by the formula [3],

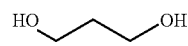

in the presence of a base, thereby obtaining a reaction mixture containing the 3-hydroxypropyl ester; and
(b) distilling the reaction mixture obtained by the step (a), under reduced pressure, thereby recovering the 3-hydroxypropyl ester as a main distillate.

11. A process according to claim 10, wherein the step (a) is conducted by putting the 1,3-propanediol into a reactor and then by intermittently or continuously adding the 2-trifluoromethylacrylic halide into the reactor.

12. A process according to claim 10, wherein the step (b) is conducted under 2,400 Pa or less.

13. A process according to claim 10, wherein the reaction mixture obtained by the step (a) is directly distilled in the step (b), without conducting a purification operation between the steps (a) and (b).

14. A process according to claim 10, wherein the step (a) is conducted by using the 1,3-propanediol in an excessive amount relative to the 2-trifluoromethylacrylic halide.

15. A process according to claim 10, wherein the step (a) is conducted by using 1–40 moles of the 1,3-propanediol per mol of the 2-trifluoromethylacrylic halide.

16. A process according to claim 10, wherein the main distillate obtained by the step (b) is washed with water.

17. A process for producing 3-hydroxypropyl ester of 2-trifluoromethyl acrylic acid, represented by the formula [1],

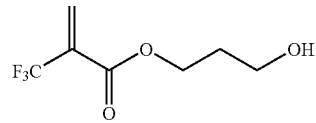

the process comprising the steps of:
(a) reacting 2-trifluoromethylacrylic halide represented by the formula [2]

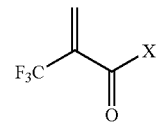

wherein X represents F or Cl, with 1,3-propanediol represented by the formula [3],

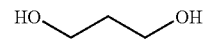

in the presence of a base by intermittently or continuously adding one equivalent of the 2-trifluoromethylacrylic halide to 1–40 equivalents of the 1,3-propanediol which has previously been put into a reactor, thereby obtaining a reaction mixture containing the 3-hydroxypropyl ester;
(b) distilling the reaction mixture obtained by the step (a) under a reduced pressure of 2,400 Pa or less, thereby recovering the 3-hydroxypropyl ester as a main distillate; and
(c) washing the main distillate obtained by the step (b) with water in the presence of a water-insoluble organic solvent.

18. A process according to claim 17, wherein the water-insoluble organic solvent of the step (c) is at least one selected from ethers, chlorine-containing solvents, and aromatic solvents.

19. A process according to claim 18, wherein the ethers are diethyl ether and diisopropyl ether, the chlorine-containing solvents are methylene chloride, chloroform and carbon tetrachloride, and the aromatic solvents are benzene, toluene and xylene.

* * * * *